United States Patent [19]
Moskovich

[11] Patent Number: 5,431,658
[45] Date of Patent: Jul. 11, 1995

[54] FACILITATOR FOR VERTEBRAE GRAFTS AND PROSTHESES

[76] Inventor: Ronald Moskovich, 1010 Constable, Mamaroneck, N.Y. 10543

[21] Appl. No.: 195,203
[22] Filed: Feb. 14, 1994
[51] Int. Cl.⁶ ............................................. A61B 17/00
[52] U.S. Cl. .......................................... 606/99; 606/90
[58] Field of Search ...................... 606/61, 90, 99, 108, 606/53; 254/98, 100

[56] References Cited

U.S. PATENT DOCUMENTS

| | | | |
|---|---|---|---|
| 3,085,786 | 4/1963 | Deuss | 254/100 |
| 3,486,505 | 12/1969 | Morrison | 606/61 |
| 3,848,601 | 11/1974 | Ma et al. | 623/17 |
| 4,066,082 | 1/1978 | Arcan et al. | 606/61 |
| 4,566,466 | 1/1986 | Ripple et al. | 623/17 |
| 4,714,469 | 12/1987 | Kenna | 623/17 |
| 4,834,757 | 5/1989 | Brantigan | 623/17 |
| 4,881,525 | 11/1989 | Williams | 623/17 |
| 4,946,378 | 8/1990 | Hirayama et al. | 606/61 |
| 5,059,194 | 10/1991 | Michelson | 606/61 |
| 5,122,130 | 6/1992 | Keller | 606/61 |
| 5,192,327 | 3/1993 | Brantigan | 606/61 |
| 5,304,119 | 4/1994 | Balaban et al. | 606/108 |

OTHER PUBLICATIONS

*Operative Orthopaedics,* pp. 1932–1934.

*Primary Examiner*—Tamara L. Graysay
*Assistant Examiner*—Scott B. Markow
*Attorney, Agent, or Firm*—Stephen C. Glazier

[57] ABSTRACT

The Moskovich facilitator facilitates the insertion of bone grafts between two vertebrae. The invention has two flat tong-like guides that distract the vertebrae as the graft slides between the two guides towards the vertebrae. The two guides have grooved surfaces to keep the graft from rotating or from slipping laterally. The two guides each have a lip to keep them from slipping too far in between the vertebrae. The two guides can be combined by an elbow piece into one part. The elbow is offset to permit impacting the graft directly on the angle of the axes of the guides. The two guides each have a notch, and the two notches hold an inserter/extractor. The screw-type inserter/extractor slowly rams the graft in between the vertebrae without impact, and slowly extracts the guides after the graft is seated.

5 Claims, 4 Drawing Sheets

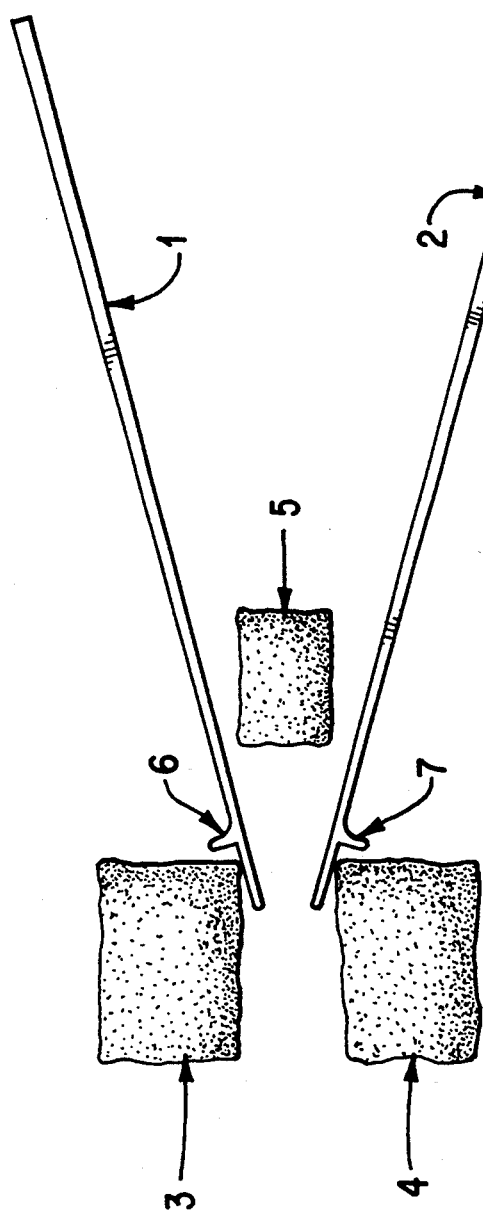
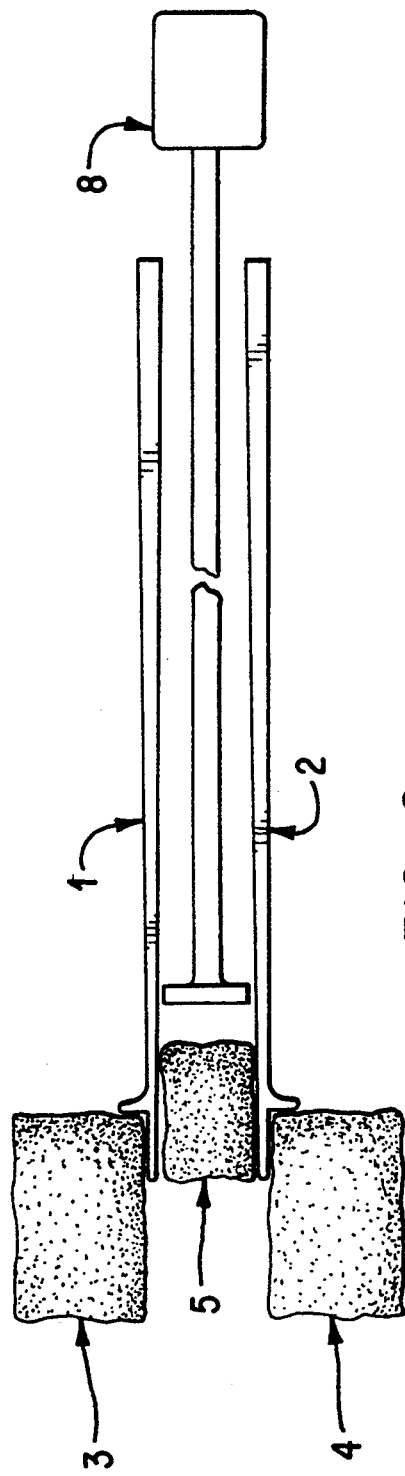

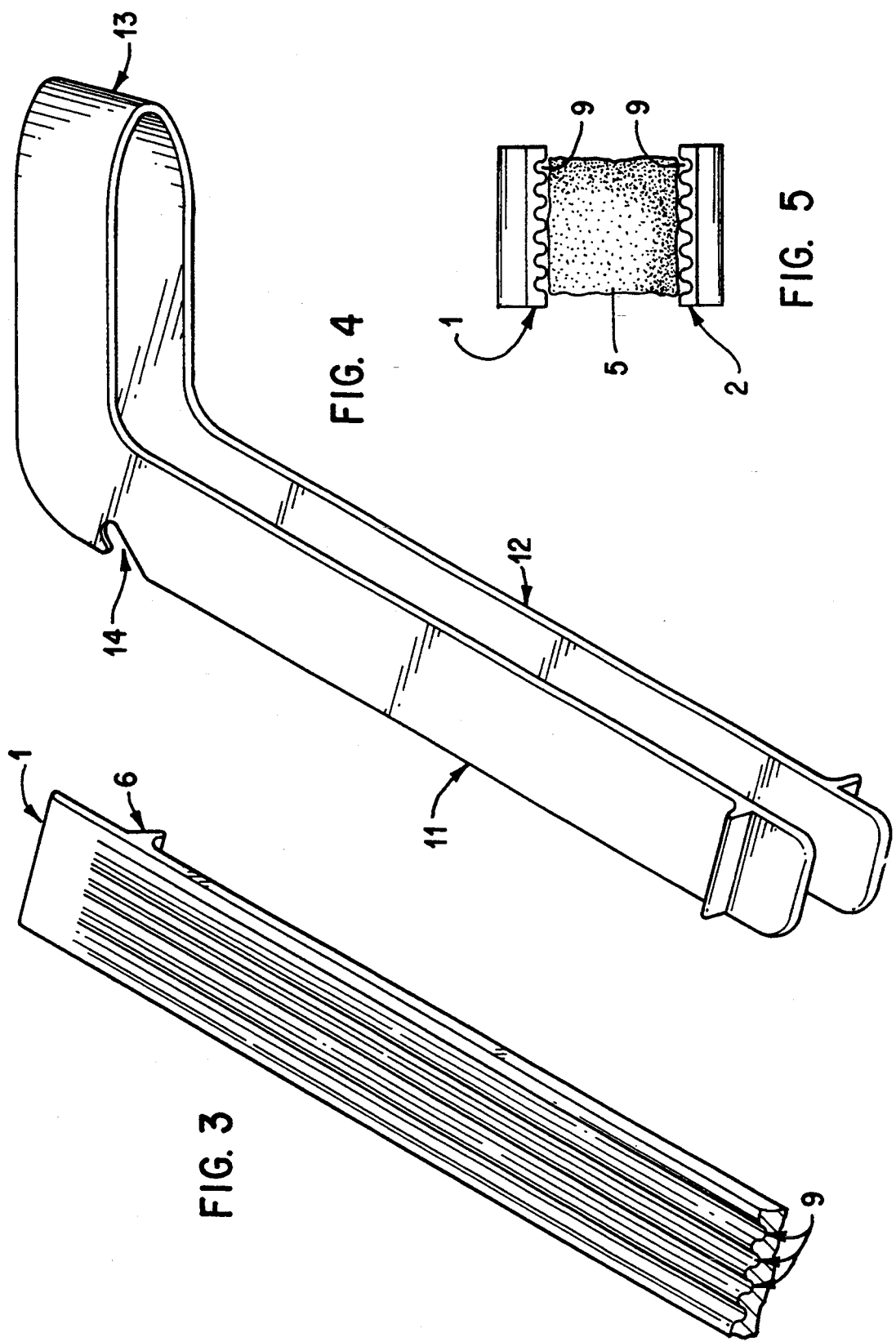

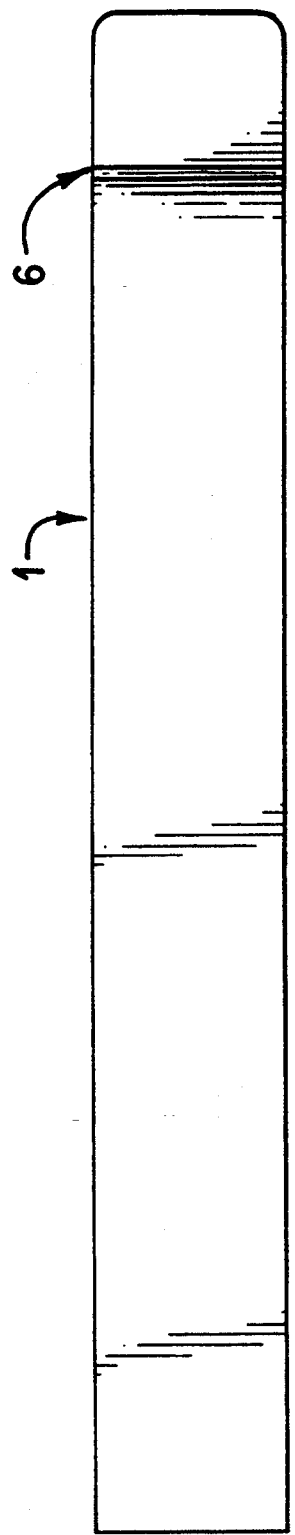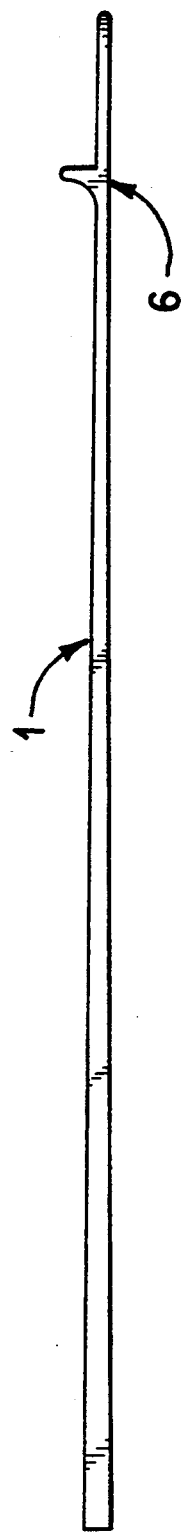
FIG. 8A
FIG. 8B

FACILITATOR FOR VERTEBRAE GRAFTS AND PROSTHESES

FIELD OF INVENTION

This invention relates to the general field of orthopaedic surgical equipment, and more specifically to the field of the insertion of bone grafts into the neck and back. Specifically, this invention includes a new tool to facilitate the insertion of a bone graft between two vertebrae. This tool is called the Moskovich facilitator.

BACKGROUND

The placement of a bone graft between the vertebrae can be quite difficult. The graft is contoured to fit into the interbody space between the vertebrae. This space may have parallel sides, or have a slight dovetailed recess for graft reception. Either a parallel-sided or a dovetailed or keystone-shaped graft would be used, depending on the shape of the corresponding interbody space. Bone grafts may be placed between the vertebral bodies following removal of the intervertebral disk (interbody grafts) or following resection of all or part of one or more vertebral bodies (vertebral reconstruction). The technique of graft insertion is similar for these two processes, differing in the length or height of the graft which is to be inserted. Both techniques may be performed more easily using the Moskovich Facilitator.

Intervertebral disk prostheses are usually designed to be inserted into the interbody space after removal of the damaged intervertebral disk. The prostheses are usually designed to be fixed in place by an interference fit and frequently have metal endplates designed for bone ingrowth. Insertion of the prosthesis is correspondingly difficult due to the precision of fit required for successful operation of the device.

The prior art for interbody graft insertion makes a small pilot hole in the anterior part of the graft and a Cloward bone tamp is screwed into the graft. Up to 40 or 50 pounds distraction is then applied by the anesthesiologist to the head halter or to the skull tongs. After a few minutes of traction, which allows for stress relaxation, the graft is gently tamped into position. The instruments are then removed and the traction weights are released.

This prior art has numerous difficulties. The bone graft is usually small and easily damaged by drilling a hole into it, or by forcing it into a tight interbody space. Also, the graft can rotate during insertion or slip sideways, which may result in injury to delicate and important structures in the neck.

Another problem with the prior art is the application of a distraction force between the vertebrae, which the prior art requires from either longitudinal traction or the use of a spreader inserted between the vertebrae. Devices which screw into the vertebrae to provide distraction have been produced. This problem is even more difficult if a dovetail-shaped graft is used. If this type of graft is inserted with too little distraction, then the result may be the development of kyphosis (that is, forward bending posture) at the fusion site, or even graft dislodgement. Also, the use of a spreader to distract the interbody space is sometimes impossible because of limited space, or may cause fracture of a vertebra by the application of concentrated force by the inserted points of the spreader. Insertion of grafts at more than one level increases the level of difficulty encountered. Insertion of thoracic or lumbar or lumbosacral interbody grafts is made more difficult by the limited physical access to the vertebrae and the difficulty of obtaining distraction to insert the graft. In the presence of degenerative disease or chronic changes where the disk space has become narrow, the problem of adequate restoration of anatomic interbody height is exacerbated.

The Moskovich facilitator allows the surgeon to safely and accurately position the graft, even when it is necessary to apply force to the graft with a mallet, while also avoiding the problems of the prior art described above. The device can also be used to insert intervertebral disk prostheses. The device (of appropriate and proportional size) may be used at any level in the spine. SUMMARY OF THE INVENTION The Moskovich facilitator facilitates the insertion of bone grafts between two vertebrae. The invention has two flat tong-like guides that distract the vertebrae as the graft slides between the two guides towards the vertebrae. The two guides have grooved surfaces to keep the graft from rotating or from slipping laterally. The two guides each have a lip to keep them from slipping too far in between the vertebrae. The two guides can be combined by an elbow piece into one part. The elbow is offset to permit impacting the graft directly on the angle of the axes of the guides. The two guides each have a notch, and the two notches hold an inserter/extractor. The screw-type inserter/extractor slowly rams the graft in between the vertebrae without impact, and slowly extracts the guides after the graft is seated.

BRIEF DESCRIPTION OF THE DRAWING

FIG. 1 shows a side view of the invention in its pair form, prior to inserting the graft.

FIG. 2 shows a side view of the invention in its pair form, after insertion of the graft with an impactor has begun.

FIG. 3 shows the grooved inside surface and the lip on the outside surface of the guide.

FIG. 4 shows the one-piece version of the invention.

FIG. 5 shows an end view of the invention with a bone graft.

FIGS. 8a and 8b show a top and side view of one of the pair of guides of the invention.

DETAILED DESCRIPTION OF THE PREFERRED EMBODIMENTS

Figure 6:
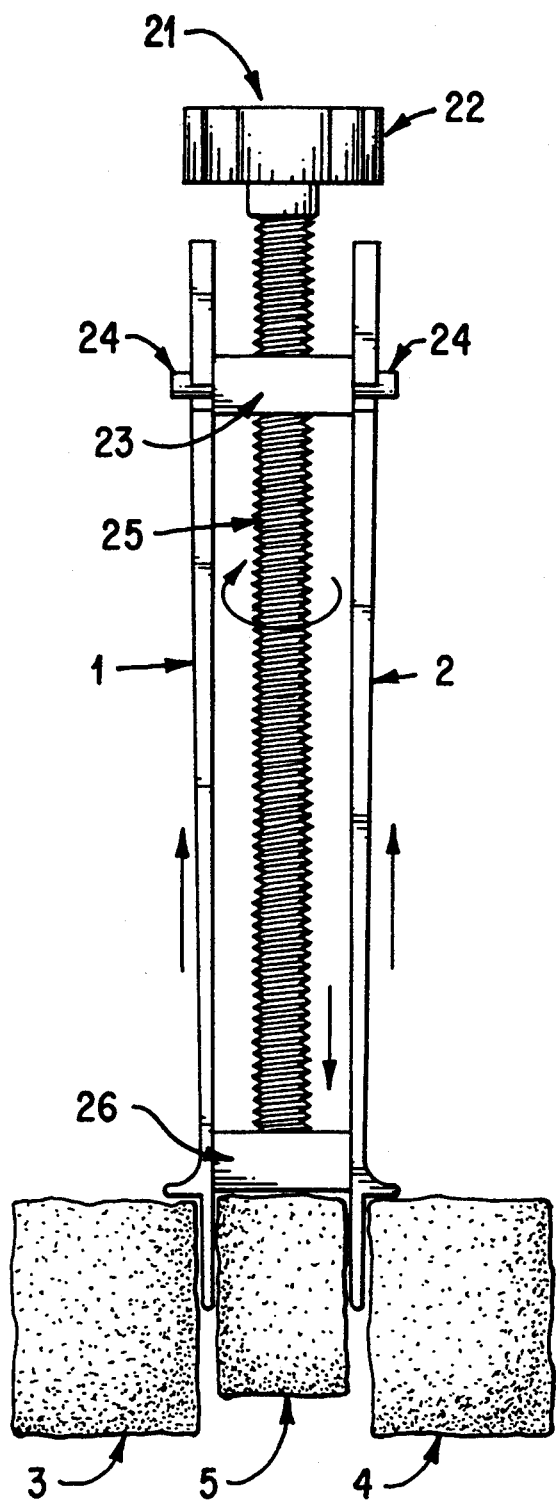
FIG. 6 shows a side view of the one piece version of the invention with the inserter/extractor.

FIG. 1 shows a side view of the invention in its pair form, prior to inserting the graft. The invention here has a pair of guides 1 and 2 inserted between two vertebrae 3 and 4. A bone graft 5 is shown between guides 1 and 2, ready for insertion between the vertebrae. Each guide 1 and 2 has a lip 6 and 7, respectively. The lip keeps each guide from entering too far in between the vertebrae, and in particular, the lip keeps each guide out of the spinal canal. The lip is at the point of maximum penetration of the guide between the vertebrae.

FIG. 2 shows a side view of the invention in its pair form, after insertion of the graft with an impactor 8 has begun.

FIG. 3 shows the grooved inside surface and the lip 6 on the outside surface of the guide 1. The grooved surface has a plurality of parallel grooves 9 running the length of the guide 1. These grooves keep the bone graft from rotating or slipping laterally during the graft's insertion. A similar function can be served by a raised curb or ridge along the inside edges of the guides 1 and 2. For convenience, FIG. 3 shows only one guide 1, but guide 2 matches guide 1.

FIG. 4 shows the one-piece version of the invention. The two guides 1 and 2 are manufactured as two guides 11 and 12 of one larger piece, by joining them by an elbow piece 13. In practice this embodiment can be made out of one piece of stainless steel or other material. The elbow 13 is offset from the axes of guides 11 and 12 to permit direct impacting of the bone graft 5 without offsetting the angle of attack of the impactor 8. A notch 14 is shown in one edge of guide 11, and a matching notch is in guide 12 but not visible here. These two notches allow for the easy mounting and use of the inserter/extractor 21. The embodiment of the invention shown in FIG. 4 also may contain parallel grooves 9 as shown in FIG. 3 and FIG. 5 (not shown in FIG. 4)

FIG. 5 shows an end view of the invention with a bone graft. The bone graft 5 is between the two guides 1 and 2, each with a plurality of grooves 9.

FIG. 6 shows a side view of the one piece version of the invention with the inserter/extractor 21. The inserter/extractor 21 has a knob 22, a threaded nut 23 with two side studs 24. The two side studs 24 fit into the two notches 14 to fix the inserter/extractor into the invention. The inserter/extractor also has a screw 25 threaded into nut 23, and a ram 26. The ram 26 is rotatably attached to the end of the screw 25 that is opposite from the knob 21. The ram is restrained by the two guides from rotating in relationship to the two guides and the graft while rotating in relationship to the screw. When the knob is turned one way, the ram pushes the graft in between the vertebrae 3 and 4, forcing the vertebrae apart just enough to accept the graft. The graft and interbody space to receive the graft are both cut so that the graft jams tightly into the interbody space between the vertebrae. When the graft jams, it can advance no further, and further turning of the knob cause the advancing ram to push the ends of the two guides 1 and 2 out from between the vertebrae.

Figure 7:
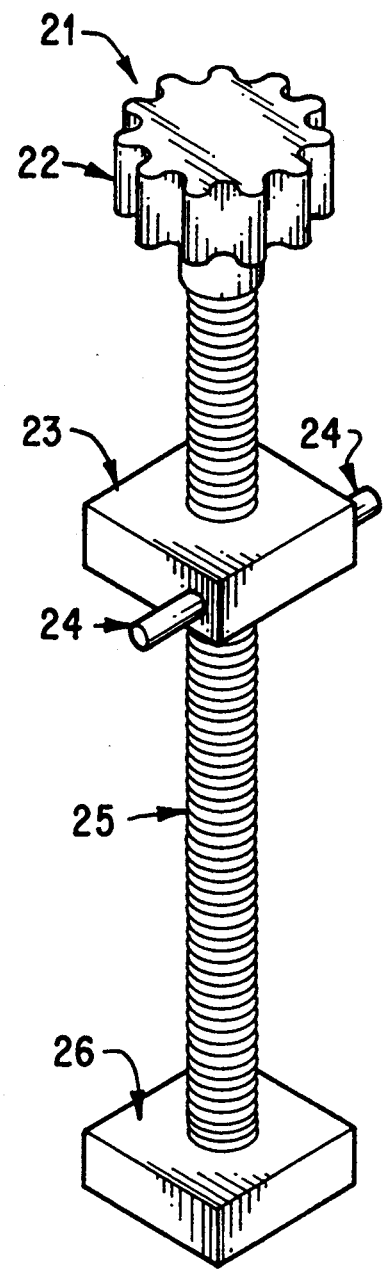
FIG. 7 shows the inserter/extractor of the invention by itself.

FIG. 7 shows the same inserter/extractor 21 of the invention by itself.

FIGS. 8a and 8d show a top and side view of one of the pair of guides of the invention. For convenience, FIG. 8a and 8b show only one guide 1, but guide 2 matches guide 1.

The embodiments illustrated and discussed in this specification are intended only to teach those skilled in the art the best way known by the inventor to make and use the invention. Nothing in the specification should be considered as limiting the scope of the present invention. Changes could be made by those skilled in the art to produce equivalent systems without departing from the invention. The present invention should only be limited by the following claims and their legal equivalents.

I claim:

1. A vertebrae graft facilitator comprising:
   (a) a graft guide with a distal end, a proximal end, a longitudinal axis, an outside surface, an inside surface, and two longitudinal edges,
   (b) a matching graft guide with a distal end, a proximal end, a longitudinal axis, an outside surface, an inside surface, and two longitudinal edges, and
   (c) an elbow piece connecting the two graft guides at the proximal end of each guide, the elbow piece extending out of a plane defined by the longitudinal axes of the two guides and extending from one of the longitudinal edges of each guide, the two guides flexibly located parallel to each other with their inside surfaces facing each other.

2. The vertebrae graft facilitator in claim 1, further comprising:
   (a) a lip on the outside surface of each guide near the distal end of each guide
   (b) a plurality of parallel grooves on the inside surface of each guide, the grooves running between the proximal end and the distal end of each guide, and
   (c) one matching notch in each of the two guides, in one longitudinal edge of each guide.

3. A vertebrae graft facilitator comprising:
   (a) a graft guide with a distal end, a proximal end, a longitudinal axis, an outside surface, an inside surface, and two longitudinal edges,
   (b) a matching graft guide with a distal end, a proximal end, a longitudinal axis, an outside surface, an inside surface, and two longitudinal edges, and
   (c) an elbow piece connecting the two graft guides at the proximal end of each guide, the elbow piece extending out of a plane defined by the longitudinal axes of the two guides and extending from one of the longitudinal edges of each guide, the two guides flexibly located parallel to each other with their inside surfaces facing each other,
   (d) a lip on the outside surface of each guide near the distal end of each guide,
   (e) a plurality of parallel grooves on the inside surface of each guide, the grooves running between the proximal end and the distal end of each guide,
   (f) one matching notch in each of the two guides, in one longitudinal edge of each guide, and
   (g) an inserter/extractor inserted in the two notches and in between the two guides, further comprising:
      (i) a knob attached to a proximal end of a screw, the screw having a longitudinal axis,
      (ii) a threaded nut screwed onto the screw,
      (iii) a pair of studs, each stud on opposite sides of the nut, and each stud inserted into one of the notches, the inserter/extractor located in between the two guides, with the proximal end of the screw near the elbow piece, and the axis of the screw aligned with the longitudinal axes of the guides, and
      (iv) a ram rotatably attached to a distal end of the screw, the ram located between the two guides.

4. A vertebrae graft facilitator comprising:
   (a) a graft guide with a distal end, a proximal end, a longitudinal axis, an outside surface, an inside surface, and two longitudinal edges,
   (b) a matching graft guide with a distal end, a proximal end, a longitudinal axis, an outside surface, an inside surface, and two longitudinal edges,
   (c) an elbow piece connecting the two graft guides at the proximal end of each guide, the elbow piece extending out of a plane defined by the longitudinal axes of the two guides and extending form one of the longitudinal edges of each guide, the two guides flexibly located parallel to each other with their inside surfaces facing each other,
   (d) one matching notch in each of the two guides, in one longitudinal edge of each guide, and (e) an inserter/extractor fixable in the two notches and in between the two guides further comprising:
  (i) a knob attached to a proximal end of a screw, the screw having a longitudinal axis,
  (ii) threaded nut screwed onto the screw,
  (iii) a pair of studs, each stud on opposite sides of the nut, and each stud inserted into one of the notches, the inserter/extractor located in between the two guides, with the proximal end of the screw near the elbow piece, and the axis of the screw aligned with the longitudinal axes of the guides, and
  (iv) a ram rotatably attached to a distal end of the screw, the ram located between the two guides.

5. A vertebrae graft facilitator comprising:
(a) a first graft guide with a distal end, a proximal end, a longitudinal axis, an outside surface, an inside surface, and an edge,
(b) a second, matching, graft guide with a distal end, a proximal end, a longitudinal axis, an outside surface, an inside surface, and an edge, the first and second graft guides flexibly located parallel to each other with their inside surfaces facing each other,
(c) one matching notch in each of the two guides, in the edge of each guide, and
(d) an inserter/extractor fixable in the two notches and in between the two guides further comprising:
  (i) a knob attached to a proximal end of a screw, the screw having a longitudinal axis,
  (ii) a threaded nut screwed onto the screw,
  (iii) a pair of studs, each stud on opposite sides of the nut, and each stud inserted into one of the notches, the inserter/extractor located in between the two guides, with the axis of the screw aligned with the longitudinal axes of the guides, and
  (iv) a ram rotatably attached to a distal end of the screw, the ram located between the two guides.

* * * * *